United States Patent [19]

Fedoseev et al.

[11] 4,148,964

[45] Apr. 10, 1979

[54] POLYCRYSTALLINE SUPERHARD MATERIAL AND METHOD OF PRODUCING THEREOF

[76] Inventors: Dmitry V. Fedoseev, ulitsa akademika Pavlova, 40, kv. 140; Boris V. Deryagin, ulitsa Vavilova, 37a, kv. 54, both of Moscow; Valentin N. Bakul, ulitsa Kirova, 34a, kv. 12, Kiev; Alexei I. Prikhna, ulitsa Vyshgorodskaya, 33, kv.20, Kiev; Valentin K. Gerasimenko, ulitsa Bolshaya Mastitskaya, 81, kv. 1, Kiev; Vladimir G. Poltoratsky, ulitsa Shamrylo, 8, kv. 39, Kiev; Jury I. Nikitin, ulitsa Krasnopolskaya, 11/13, kv. 41, Kiev; Stanislav P. Vnukov, ulitsa Butlerova, 10, kv. 156; Valentin P. Varnin, Orlikov pereulok, 6/1, kv. 57, both of Moscow, all of U.S.S.R.

[21] Appl. No.: 760,902

[22] Filed: Jan. 21, 1977

[51] Int. Cl.² .......................... B32B 5/16; B32B 9/04
[52] U.S. Cl. .................................... 428/403; 428/538; 428/543; 106/55; 264/332
[58] Field of Search ............... 428/403, 404, 538, 543; 106/55, 56, 43

[56] References Cited

U.S. PATENT DOCUMENTS 3,852,078  12/1974  Wakatsuki et al. .................... 106/55

FOREIGN PATENT DOCUMENTS 784705  10/1957  United Kingdom ...................... 106/55
990818   5/1965  United Kingdom.

OTHER PUBLICATIONS

Samsonov et al., "Boron Carbonitride as a High-temperature, Electrically Insulating Refractory Material", in Chemical Abstracts, vol. 78, 127866c (1973), p. 228.
Andreeva et al., "Electrically Insulating Materials for Linings and Holders of High-pressure Chambers", in Chemical Abstracts, vol. 81, 160911y, (1974), p. 514.

*Primary Examiner*—George F. Lesmes
*Assistant Examiner*—R. Eugene Varndell, Jr.
*Attorney, Agent, or Firm*—Robert E. Burns; Emmanuel J. Lobato; Bruce L. Adams

[57] ABSTRACT

The proposed polycrystalline superhard material comprises sintered particles of cubic boron nitride coated over the whole surface thereof with a layer of a crystalline compound of the chemical formula $B_xN_yC_z$, where x, y and z can assume any value from 0 to 1, said compound binding together the particles of the cubic boron nitride.

According to the present invention the proposed material is produced in the following way: particles of cubic boron nitride are placed in a flow of a gas containing carbon for a carbon layer 1–100 Å thick to be built up on the whole surface of said particles. Then the particles of cubic boron nitride with the carbon layer built up over the whole surface of the particles are subjected to sintering at a temperature and under a pressure corresponding to the region of thermodynamic stability of cubic boron nitride.

The herein-proposed material is highly uniform and features mechanical properties superior to those of the known cubic boron nitride materials. Thus, for example, under the identical conditions of cutting, durability of cutters made from the proposed material is 2–5 times higher than that of the cutters made from the known material based on cubic boron nitride.

1 Claim, 2 Drawing Figures

POLYCRYSTALLINE SUPERHARD MATERIAL AND METHOD OF PRODUCING THEREOF

BACKGROUND OF THE INVENTION

The present invention relates to superhard materials based on cubic boron nitride, said material being used for manufacturing water-resistant inserts for cutting, dressing, and drilling tools, and for wire-drawing dies.

Known polycrystalline superhard materials based on cubic boron nitride can be classified into two groups. In the materials belonging to the first group the crystals of cubic boron nitride are strongly interconnected due to self-binding, i.e. by virtue of diffusion processes taking place in the zone of contact of the particles being sintered, without a binder (accepted Japanese Patent Application No. 49-30357). In the materials belonging to the second group the crystals of cubic boron nitride are interconnected by a binder.

U.K. Pat. No. 990,818 teaches a number of metals such as nickel, chromium, zirconium, cobalt, manganese, copper, rhenium, titanium, and molybdenum as a binder in a polycrystalline superhard material based on cubic boron nitride.

Polycrystalline superhard materials are known which contain, in addition to crystals of cubic boron nitride, crystals of diamond; as a binder use is made of metals (accepted Japanese Patent Application No. 43-30409), refractory materials such as borides and oxides of magnesium and calcium (French Pat. No. 2,201,268).

According to the known methods of producing polycrystalline superhard materials (see, for example, U.K. Pat. No. 990,818), it is possible to produce compact strong polycrystalline materials by sintering particles of boron nitride at high temperatures within the range from 1,200° to 2,400° C. and under pressures above 75 kbar.

Polycrystals produced by the known method exhibit relatively low wear resistance when tested on hardened steels in a cutting tool under dynamic loads (impact strength). This is caused by the fact that no strong bond is formed between the neighbouring crystals of cubic boron nitride in the process of sintering when pure powders of cubic boron nitrides are used.

A method is also known of producing polycrystalline superhard material (accepted Japanese Patent Application No. 43-30409) from a mixture of graphite powder, metallic powder, and crystals of cubic boron nitride under pressures above 50 kbar and at a temperature of 1,200° C. in the region of diamond formation; in this method a binder-metal catalyzes the formation of diamond, carbon-containing material transforms into diamond, particles of diamond and cubic boron nitride are fixed in the binder-metal.

A disadvantage inherent in the above-cited material is its low thermal stability caused by the presence of the remaining reaction products and the binder-metal.

Polycrystals produced by this known method can be used only as abrasives but not as a cutting tool.

Likewise a polycrystalline superhard material is known in the art which is produced from a mixture of powders of cubic boron nitride and boron carbide, the latter component amounting to 25 wt.% in the resulting material (U.K. Pat. No. 975,316). The material is prepared under a pressure equal to at least 15 kbar and at a temperature of 1,050° C.

This known method is disadvantageous in that the resulting material is fragile and therefore cannot be used in a cutting tool under conditions of dynamic loads when working heardened difficult-to-work steels and alloys.

Besides, the known method does not ensure highly uniform material, since simple mechanical stirring of the initial components, cubic boron nitride and boron carbide that have different densities makes it absolutely impossible to obtain strictly uniform distribution of particles of various materials, even in the case when one of the components is taken in a highly dispersed state. Heterogeneity of the material and non-uniform distribution of the components in the bulk of the material deteriorates its mechanical characteristics, in particular, resistance to impact thermal and mechanical loads.

SUMMARY OF THE INVENTION

It is an object of the invention to eliminate the above-cited disadvantages.

It is an object of the invention to provide such polycrystalline superhard material from cubic boron nitride which will possess improved mechanical properties, in particular, high wear-resistance.

Another object of the invention is to provide a method of producing a polycrystalline superhard material from cubic boron nitride, which will possess improved mechanical properties, in particular, high wear-resistance.

Said objects are accomplished by a polycrystalline superhard material derived from cubic boron nitride and produced by sintering particles at a temperature no less than 1,600° C. and under a pressure no less than 50 kbar; according to the present invention, each particle of cubic boron nitride is coated over the whole surface with a layer of a crystalline compound of the formula $B_xN_yC_z$, where x, y and z can assume any value from 0 to 1, said compound binding the particles of cubic boron nitride.

DESCRIPTION OF THE INVENTION

It is expedient, according to the present invention, that the carbon contained in the crystalline compound of the formula $B_xN_yC_z$ amount to 0.1–10 wt.% of the total weight of the polycrystalline material.

The polycrystalline superhard material proposed in the present invention is highly uniform and it displays mechanical properties superior to those of the known materials from cubic boron nitride. Thus, for example, under identical conditions of cutting, resistance of cutters made from the herein proposed material is 2–5 times higher than that of the cutters from the hitherto known materials based on cubic boron nitride.

According to the present invention, it is expedient that the polycrystalline superhard material from cubic boron nitride be produced by a method wherein the particles of cubic boron nitride are placed in a flow of a gas containing carbon in order to build up a layer 1–100 Å thick over the whole surface of the particles, and then said particles are sintered at temperatures and pressures corresponding to the region of thermodynamic stability of cubic boron nitride.

To provide conditions enabling phase rearrangement of carbon in a boundary layer, it is expedient, according to the present invention, to build up a carbon layer in a flow of gaseous hydrocarbons under a pressure of from 0.1 to 760 mm Hg and at a temperature of from 700° to 1,100° C.

It is expedient, according to the present invention, to carry out sintering of particles of cubic boron nitride under a pressure above 50 kbar and at a temperature above 1,600° C.

For a more rapid and uniform building up of a carbon layer on the surface of particles of cubic boron nitride under similar conditions, methane is used as a gaseous hydrocarbon.

Other objects and advantages of the present invention will become more fully apparent from the following detailed description of the herein-proposed polycrystalline superhard material from cubic boron nitride, the method of producing thereof, and the accompanying drawings wherein.

Figure 1:
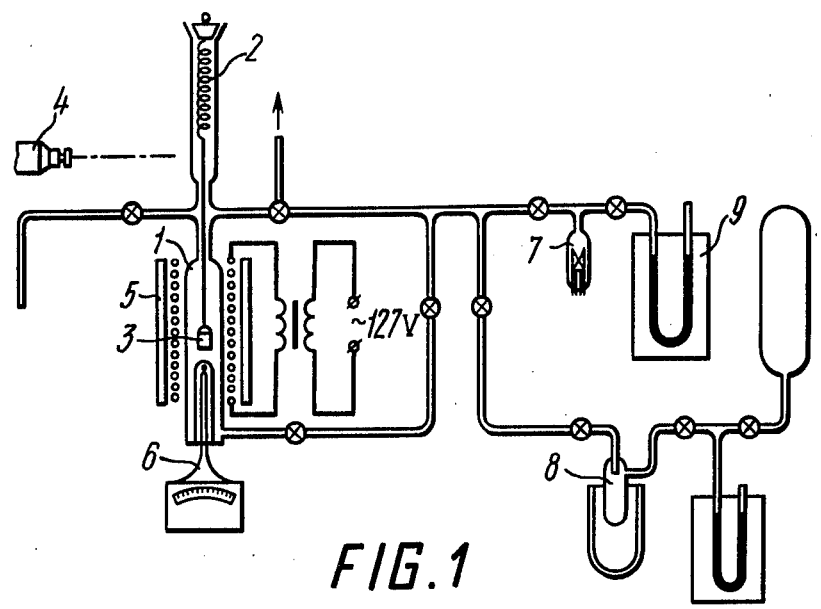
FIG. 1 is a schematic diagram of an apparatus for building up a carbon layer on particles of cubic boron nitride.

Polycrystalline superhard material proposed in the present invention comprises particles of cubic boron nitride sintered at a temperature no less than 1,600° C. and under a pressure no less than 50 kbar, each particle, according to the present invention, being coated over the whole surface with a layer of a crystalline compound of the chemical formula $B_xN_yC_z$, where x, y and z can assume any value from 0 to 1. We have found experimentally that in the lower portion of the layer x and y are equal to 1 and z equals 0, while in the upper portions of the layer $z=1$, x and $y=0$.

We have also found that best characteristics are displayed by the material, wherein the crystalline compound thereof with the chemical formula $B_xN_yC_z$ contains carbon in the amount of 0.1–10 wt.% of the total weight of the polycrystalline superhard material. It has been established experimentally that extremely high pressures are required for producing material wherein the crystalline compound thereof contains carbon in amounts differing from those claimed by us.

According to the present invention the herein-proposed polycrystalline superhard material is produced in the following way. Particles of cubic boron nitride 0.3–60μ in size are placed in a flow of a gas containing carbon, for example, gaseous hydrocarbon or, more precisely, methane or acetylene, in order that a carbon layer 1–100 Å thick be built up over the whole surface of these particles. The thickness of the carbon layer cannot be less than 1 Å, i.e. one atomic dimension (even a thickness on the order of 1 Å is actually the result of averaging). At thicknesses exceeding 100 Å it is difficult to accomplish phase transition of graphite into diamond, the upper layer of coating at such thicknesses being graphite without a catalyst under pressures of up to 150 kbar and appropriate temperatures.

We have established that it is expedient to build up a carbon layer on the particles of cubic boron nitride under 0.1 to 760 mm Hg and at 700° to 1100° C., since these layer building-up conditions ensure a structure of the transition layer, most favorable for the phase transformation.

After the formation of the coating layer, the particles of cubic boron nitride are sintered, the result being a polycrystalline superhard compound, wherein each particle of cubic boron nitride is coated with a layer of a crystalline compound formed in the process of sintering, the chemical formula of the compound being $B_xN_yC_z$, where x, y and z can assume any value from 0 to 1.

Investigations have shown, that it is just the formation of this new crystalline compound which strongly bonds together the sintered particles of cubic boron nitride into a uniform compact product, whereby the resulting material is rendered more wear-resistant.

It should be mentioned that in case of mechanical intermixing of particles of cubic boron nitride and of carbon-containing material, for example, graphite, and subsequent sintering thereof, as is described in the above-cited Japanese Accepted Application No. 43-30409, a crystalline compound of the chemical formula $B_xN_yC_z$ is not formed.

A carbon layer with a diamond-graphite structure is built up on the surface of particles of cubic boron nitride by way of epitaxial growing, i.e. in such a manner that the substrate structure and its surface forces play an essential role. During the process of epitaxial growing, a diamond-graphite layer is built up directly on the surface of cubic boron nitride particles from the above-cited hydrocarbons at a temperature of from 700° to 1,100° C. and under a pressure of from 0.1 mm Hg to atmospheric. Since the parameters of the crystal lattice of cubic boron nitride are close to those of a diamond (the difference does not exceed 1.5%), the carbon contained in the gas flow is crystallized under the effect of surface forces on the surface of cubic boron nitride particles in the form of diamond and graphite. The initial layers of the crystallizing carbon consist mainly of diamond; then, graphite is crystallized along with diamond; and finally, graphite alone as a thermodynamic form of carbon grows on the particles of cubic boron nitride in the flow of gaseous hydrocarbon. The ratio between diamond and graphite in the built up layers is essentially dependent on the composition of the carbon-containing gas, as well as on the temperature and pressure at which the building-up is conducted. Thus, dilution of hydrocarbon gas with hydrogen makes it possible to obtain more extended diamond layers. Therefore, for obtaining a diamond-graphite layer, it is most expedient to use methane containing one carbon atom per four hydrogen atoms. Methane is the most slow to decompose among all other hydrocarbons in the above-cited temperature and pressure ranges. This property of methane makes it most suitable for preliminary building up of carbon on particles of cubic boron nitride. Lower diamond and graphite growth rate from methane than from other hydrocarbons ensures uniform building up of the diamond-graphite layer over the entire depth of the layer of the cubic boron nitride particles. Thus, the use of methane, all other conditions being equal, allows a carbon layer to be built up on a larger portion of the initial particles of cubic boron nitride.

Experiments have shown that upon epitaxial growing of carbon on the sites of the surface of cubic boron nitride particles, where carbon is built up in a diamond form, a strong chemical bond is formed. On those sites of the particles being treated where carbon is grown in the graphite form, the graphite has a structure ordered with respect to the cubic boron nitride substrate, this structure being slightly distorted by insertion of boron and nitrogen atoms caused by diffusion of these elements under the conditions of the building-up process. On the one hand, such a structure of the built up carbon layer provides coherent sintering of the particles under the effect of high temperatures and pressures when the particles of cubic boron nitride are brought closer together. On the other hand, this structure is kinetically more mobile with respect of rearrangement of graphite into other forms.

When the sintering process is conducted at high temperatures (1,600° C. and higher), carbon diffuses into the surface layers of the cubic boron nitride particles, and nitrogen and boron atoms diffuse into the carbon layer. Due to the fact that the atomic radii of these elements are close in value, these inclusions cause neither noticeable distortions of crystal lattices nor arising of stresses.

The diffusion nature of the sintering processes ensures a smooth change in the composition and properties of the built up transition layers. Since the particles of cubic boron nitride are monocrystals and, consequently, are anisotropic, the presence of transition layers influences the properties of particles with different orientation in such a way that the mechanical properties of the material obtained after sintering are considerably improved. In addition, it should be mentioned, that crystalline compounds with a structure described by the chemical formula $B_zN_yC_z$ are known to possess valuable physical properties, in particular, high resistance to impact thermal and mechanical effects.

The following results have been obtained when investigating polycrystalline superhard highly uniform material proposed in the present invention.

X-ray diffraction patterns of cubic boron nitride powders sintered at high pressures and temperatures, after a carbon layer has been deposited on them, reveal lines which cannot be assigned to any of the crystalline modifications of boron nitride or carbon. These lines are not observed on X-ray diffraction patterns of the initial and built-up powders either, which allows a conclusion to be made about a specific crystalline structure of the binding layers. Evidently, from crystallographic standpoint, these layers consist of several types of structures possible in the boron-nitrogen-carbon system. The novel lines are close to those present on X-ray diffraction patterns of carbide or carbon from the Crater Ries. However, since the amount of the built-up carbon is small and close to the sensitivity level of the X-ray method used, these lines with a relatively high intensity cannot be assigned to the pure carbon phase. Therefore, it is natural to suppose that, in the course of sintering, the carbon atoms from the carbon layer penetrate into the surface layers of boron nitride particles changing their composition and structure and ensuring coherent sintering of the particles of cubic boron nitride.

Thus, a novel compound of the chemical formula $B_xN_yC_z$, possessing high thermostability and strength, is formed, according to the method proposed in the present invention, due to the specific feature of the transition diamond-graphite layer. This layer is strictly oriented and can accelerate the formation of the above-cited novel compound. The thickness of the built up carbon layer, found to be 1 to 100 Å, also favors the acceleration of the reaction between cubic boron nitride with the diamond-graphite layer under the conditions of sintering, namely at temperatures and pressures corresponding to the region of thermodynamic stability of cubic boron nitride (above 1,600° C. and 50 kbar).

The carbon layer of the diamond-graphite structure, built up at 700° to 1,100° C. under 0.1 to 760 mm Hg, fills the space between the particles of cubic boron nitride under compression and then under the effect of high temperature. This diminishes lattice defects, strengthens the bond, and, consequently, makes the polycrystalline superhard highly uniform material stronger.

The method of producing polycrystalline material proposed in the present invention is accomplished on apparatus described below.

An apparatus for building up a carbon layer on crystals of cubic boron nitride (FIG. 1) contains a silica reactor 1 and a spring quartz balance 2. A cup 3, where initial crystals of cubic boron nitride are placed, is introduced into the reactor with the help of a silica thread. A change in the weight of the initial crystals is recorded by a cathetometer 4. Reactor 1 is heated by a furnace 5 with ohmic heating. The chromel-alumel thermocouple 6 located in a silica pocket of the reactor is used for measuring the reactor temperature. Vacuum is created by a mercury diffusion pump and a pre-evacuation pump (not shown on the figure). Pressure in reactor 1 is measured by a thermocouple tube 7 with the aid of a vacuum gauge (not shown in the Figure). Before building up, methane (or any other carbon-containing gas) is fed into a trap 8 cooled with liquid nitrogen and then into reactor 1. Methane pressure is measured with V-shaped pressure gauge 9.

The initial cubic boron nitride crystals are weighed on a microanalytical balance and then placed into reactor 1 in cup 3. The reactor is evacuated down to a residual pressure of $10^{-4}$ mm Hg, after which methane or other carbon-containing gas is passed through the reactor, the temperature and pressure of the gas corresponding to the chosen parameters of the building-up process.

As the building-up process goes on, the weight of cup 3 increases, this being registered by cathetometer 4. A weight increment corresponds to the weight of the built up layer. The layer thickness is determined from a simple weight dependence. The building-up process is stopped when the thickness attains a required value within the range of from 1 to 100 Å.

Figure 2:
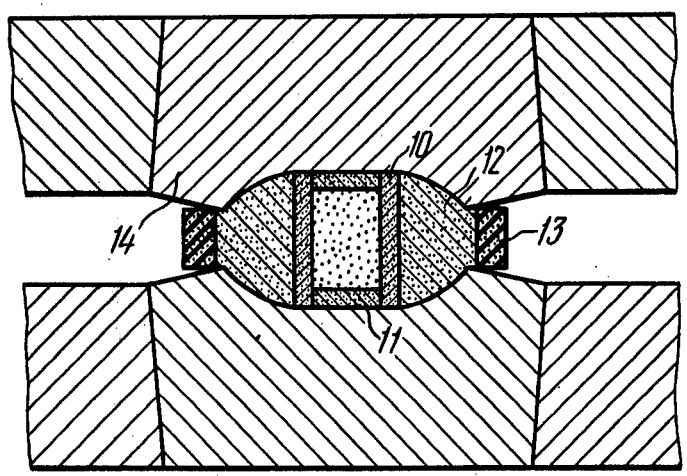
FIG. 2 shows a longitudinal sectional view of a device for creating a high pressure and a high temperature, adapted for sintering particles of cubic boron nitride with a carbon layer built up thereon.

The crystals of cubic boron nitride are sintered with the built up carbon layer in a device for creating a high pressure and a high temperature. One of such devices is shown in FIG. 2.

The crystals of cubic boron nitride with the carbon layer built up thereon are placed into a tubular graphite heater 10; the heater is closed from both sides by graphite discs 11 and put into a container 12 made of lithographic stone with a rubber sleeve on it. Then the container is placed in the space defined by recesses in two oppositely arranged dies 14 made of a hard alloy. Pressure is applied to the dies with the help of a press. When the pressure inside graphite heater 10 attains the required value (50 kbar and more), electric current is passed through the dies and the graphite heater. The contents of the heater are heated by the electric current up to the required temperature (1,600° C. and higher). The pressure and temperature attained are kept for a period of ½ to 2 minutes, after which the current is switched off, the pressure is relieved and a small cylinder consisting of strongly interconnected crystals of cubic boron nitride is separated from the heater and container destroyed during the compression.

The material proposed herein has improved mechanical properties due to high uniformity of the structure. This uniformity can be controlled by various methods of chemical and structural analysis. Elemental composition of the material can be identified either by methods of chemical analysis or by microanalysis. The absence of separate crystal formations of carbon can be ascertained by electron microdiffraction methods. As was pointed out, no other method makes it possible to ensure uniformity of the structure and preclude the formation of clusters of carbon particles.

EXAMPLE 1

A powder of cubic boron nitride with grain size $5/3\mu$ is weighed and plated into a reactor which is evacuated and then heated up to 950° C. Methane is passed over the powder under a pressure of 20 mm Hg, and a carbon layer is allowed to build up. Two graphite electrodes are put into the powder and a change in the electric resistance of the powder between the electrodes, as the carbon layer deposition goes on, is controlled.

The initial value of electric resistance is 10 megohm. During the building-up process, the resistance of the powder falls as a result of graphite depositing on the surface of the particles of cubic boron nitride powder. When the resistance value becomes 0.06 megohm, the building-up process is stopped, the powder is extracted from the reactor and weighed. The thickness of the deposited layer is found equal to 25 Å from the weight increment and known specific surface of the cubic boron nitride powder.

The graphite fraction in the built up layer is determined by the ratio $\Delta m/m_o = 1\%$, where $\Delta m$ is carbon content in the layer; $m_o$ is the amount of cubic boron nitride.

Said powder of cubic boron nitride with an epitaxially grown carbon layer 25 Å thick is placed into a tubular graphite heater 5 mm long with the outer and inside diameter of 7 and 4 mm; respectively. The powder is covered from both sides with graphite discs.

The reaction vessel is subjected for ½ minute to a pressure of 80 kbar and temperature of 2,300° C.

As a result, a superhard polycrystalline compact material is obtained in the form of a cylinder, 3.5 mm in diameter and 4 mm long.

The sample weight is 0.5 carat.

The polycrystalline element obtained is mechanically secured in a holder and treated on a diamond-electrolytic machine. A blade cutting tool is thus produced.

Tests of the cutters from the polycrystalline superhard material produced under the above-cited conditions have shown that in the process of working a cylindrical item from hardened steel, grooves being cut on the item for making its surface discontinuous, wear-resistance with respect to the back face is $h_3 = 0.4$ mm at an operation time of 200 min, the rate of cutting being $V = 100$ m/min, longitudinal feed $S = 0.084$ mm/rotation, and depth $l = 0.15$ mm.

EXAMPLE 2

A carbon layer is built on particles of cubic boron nitride with grain size $5/3\mu$ under the conditions similar to those described in Example 1 with methane pressure of 0.5 mm Hg, the thickness of the layer obtained being 8 Å ($\Delta m/m = 0.3\%$). The powder is sintered by following the procedure described in Example 1 under 77 kbar.

A cutter from the polycrystalline superhard material obtained has wear-resistance of 80 min when being tested mechanically under the conditions set forth in Example 1.

EXAMPLE 3

A carbon layer is deposited on particles of cubic boron nitride with grain size $5/3\mu$ under the conditions similar to those described in Example 1 with methane pressure of 150 mm Hg, the thickness of the layer obtained being 82 Å ($\Delta m/m = 3.3\%$). The powder is sintered by following the procedure described in Example 1 under 65 kbar.

A cutter from the polycrystalline superhard material obtained has wear-resistance of 180 min when being tested mechanically under the conditions set forth in Example 1.

EXAMPLE 4

A carbon layer is built on particles of cubic boron nitride with grain size $5/3\mu$ under the conditions similar to those described in Example 1 at a pressure of 650 mm Hg, the thickness of the layer obtained being 100 Å ($\Delta m/m = 4\%$). The powder of cubic boron nitride is sintered by following the procedure described in Example 1 at 2,000° C. and 60 kbar.

A cutter from the polycrystalline superhard material obtained has wear-resistance of 90 min. when being tested mechanically under the conditions set forth in Example 1.

EXAMPLE 5

A carbon layer is built on particles of cubic boron nitride with grain size $5/3\mu$ under the conditions similar to those described in Example 1 with methane pressure of 25 mm Hg and at a temperature of 780° C., the thickness of the layer obtained being 30 Å. The powder of cubic boron nitride is sintered by following the procedure described in Example 1, at 1,800° C. and 60 kbar for 2 minutes.

A cutter from the polycrystalline superhard material obtained has wear-resistance of 80 min. when being tested under the conditions set forth in Example 1.

EXAMPLE 6

A carbon layer is built on particles of cubic boron nitride with grain size $5/3\mu$ under the conditions similar to those described in Example 1 with methane pressure of 30 mm Hg and at a temperature of 1,050° C., the thickness of the layer obtained being 41 Å. The powder of cubic boron nitride is sintered by following the procedure described in Example 1 at 2,200° C. and 65 kbar.

A cutter from the polycrystalline material obtained has wear-resistance of 100 min. when being tested under the conditions set forth in Example 1.

EXAMPLE 7

A carbon layer is built on particles of cubic boron nitride with grain size $5/3\mu$ under the conditions similar to those described in Example 1 with methane pressure of 20 mm Hg at a temperature of 960° C., the thickness of the layer obtained being 25 Å ($\Delta m/m = 1\%$). The powder of cubic boron nitride is sintered by following the procedure described in Example 1 at 1600° C. and 50 kbar for 1 minute. Wear-resistance of the cutter is 70 minutes.

EXAMPLE 8

A carbon layer is built on particles of cubic boron nitride with grain size $5\mu$ under the conditions similar to those described in Example 1 with methane pressure of 20 mm Hg and at a temperature of 960° C., the thickness of the layer obtained being 25 Å. The powder of cubic boron nitride is sintered by following the procedure described in Example 1 at 2,700° C. and 90 kbar for 5 seconds.

A cutter from the polycrystalline superhard material obtained has a wear-resistance of 90 min. when being tested under the conditions set forth in Example 1.

EXAMPLE 9

A carbon layer is built on particles of cubic boron nitride with grain size 40/60μ under the conditions similar to those described in Example 1 with methane pressure of 0.5 mm Hg at a temperature of 960° C., the thickness of the layer obtained being 1 Å. The powder is sintered by following the conditions described in Example 1 at 2,250° C. and 80 kbar for 1 minute.

A cutter from the polycrystalline material obtained has wear-resistance of 80 min. when being tested under the conditions set forth in Example 1.

EXAMPLE 10

A carbon layer is built on particles of cubic boron nitride with grain size 40/60μ under the conditions similar to those described in Example 1 with methane pressure of 150 mm Hg and at a temperature of 960° C., the thickness of the layer obrained being 25 Å ($\Delta m/m = 0.1\%$). The powder of cubic boron nitride is sintered at 2,400° C. and 80 kbar for 1 minute.

A cutter from the polycrystalline superhard material obtained has a wear-resistance of 150 min. when being tested under the conditions set forth in Example 1.

EXAMPLE 11

A carbon layer is built on particles of cubic boron nitride with grain size 40/60μ under the conditions similar to those described in Example 1 with methane pressure of 700 mm Hg and at a temperature of 960° C., the thickness of the layer obtained being 96 Å. The powder of cubic boron nitride is sintered by following the procedure described in Example 1 at 2,300° C. and 77 kbar.

A cutter from the polycrystalline material obtained has a wear-resistance of 80 min. when being tested under the conditions set forth in Example 1.

EXAMPLE 12

A carbon layer is built on particles of cubic boron nitride with grain size 60/40μ under the conditions similar to those described in Example 1 with methane pressure of 150 mm Hg and a temperature of 720° C., the thickness of the layer obtained being 30 Å. The powder of cubic boron nitride is sintered by following the procedure described in Example 1 at 2,800° C. and 80 kbar for 1 minute.

A cutter from the material obtained has a wear-resistance of 80 min when being tested under the conditions set forth in Example 1.

EXAMPLE 13

A carbon layer is built on particles of cubic boron nitride with grain size 60/40μ under the conditions similar to those described in Example 1 with methane pressure of 150 mm Hg at a temperature of 1100° C., the thickness of the carbon layer obtained being 32 Å. The powder is sintered by following the procedure described in Example 1 at 2,300° C. and 80 kbar for 2 minutes.

A cutter from the material obtained has a wear-resistance of 90 min. when being tested under the conditions set forth in Example 1.

EXAMPLE 14

A carbon layer is built on particles of cubic boron nitride with grain size 60/40μ under the conditions similar to those described in Example 1 with methane pressure of 150 mm Hg and a temperature of 960° C., the thickness of the layer obtained being 25 Å. The powder of cubic boron nitride is sintered by following the procedure described in Example 1 at 1,800° C. and 51 kbar for 1 minute.

A cutter from the material obtained has a wear-resistance of 80 min. when being tested under the conditions set forth in Example 1.

EXAMPLE 15

A carbon layer is built on particles of cubic boron nitride with grain size 60/40μ under the conditions similar to those described in Example 1 with methane pressure of 150 mm Hg and at a temperature of 960° C., the thickness of the carbon layer obtained being 25 Å. The powder of cubic boron nitride is sintered by following the procedure described in Example 1 at 2,700° C. and 90 kbar for 5 seconds.

A cutter from the polycrystalline material obtained has a wear-resistance of 90 min. when being tested under the conditions set forth in Example 1.

EXAMPLE 16

A carbon layer is built on particles of cubic boron nitride with grain size 60/40μ in a flow of acetylene under the conditions similar to those described in Example 1 with acetylene pressure of 200 mm Hg and at a temperature of 750° C., the thickness of the carbon layer obtained being 80 Å ($\Delta m/m = 3.2\%$). The powder of cubic boron nitride is sintered by following the procedure described in Example 1 at 2,300° C. and 80 kbar.

A cutter from the polycrystalline material obtained has a wear-resistance of 80 min. when being tested under the conditions set forth in Example 1.

EXAMPLE 17

A carbon layer is built on particles of cubic boron nitride with grain size 60/40μ in a flow of acetylene under the conditions similar to those described in Example 1 with acetylene pressure of 200 mm Hg at a temperature of 800° C., the thickness of the carbon layer obtained being 94 Å. The powder of cubic boron nitride is sintered by following the procedure described in Example 1 at 2,300° C. and 80 kbar.

A cutter from the polycrystalline material obtained has a wear-resistance 70 min. when being tested under the conditions set forth in Example 1.

EXAMPLE 18

A carbon layer is built on particles of cubic boron nitride with grain size 1/0μ under the conditions similar to those described in Example 1 with methane pressure of 20 mm Hg at a temperature of 960° C., the thickness of the carbon layer being 24 Å ($\Delta m/m = 5\%$). The powder of cubic boron nitride is sintered by following the procedure described in Example 1 at 2,300° C. and 80 kbar.

A cutter from the crystalline material obtained has a wear-resistance of 90 min. when being tested under the conditions pointed out in Example 1.

EXAMPLE 19

A carbon layer is built on particles of cubic boron nitride with grain size 40μ under the conditions similar to those described in Example 1 with methane pressure of 150 mm Hg and at a temperature of 960° C., the thickness of the carbon layer obtained being 80 Å. The powder is sintered by following the procedure described in Example 1 at 2,300° C. and 77 kbar.

A cutter from the polycrystalline material obtained has a wear-resistance of 90 min. when being tested under the conditions pointed out in Example 1.

What we claim is:

1. A polycrystalline superhard material of cubic boron nitride, comprising particles of cubic boron nitride of about 0.3 to 60 microns sintered at a temperature of at least 1600° C., under pressure of no less than 50 kbar, said particles of cubic boron nitride being coated over their entire surface with a layer of about 1 to 100 Å thickness of crystalline compounds of the chemical formula $B_xN_yC_z$ wherein x, y & z can assume any value from 0 to 1 with the proviso that the crystals of said coated layer adjacent to said boron nitride have the above formula wherein x and y approach 1, and z approaches 0, while the compounds in said coating layer distal to said boron nitride particles have the above formula wherein x and y each approach 0, and z approaches 1 and wherein said compounds bond said particles of cubic boron nitride with each other, and the carbon contained in said crystalline is about 1.0 to 10% by weight of the total weight of the polycrystalline material.

* * * * *